(12) United States Patent
Dakka et al.

(10) Patent No.: US 10,011,538 B2
(45) Date of Patent: Jul. 3, 2018

(54) METHOD OF MAKING AROMATIC HYDROCARBONS

(71) Applicant: ExxonMobil Chemical Patents Inc., Baytown, TX (US)

(72) Inventors: Jihad M. Dakka, Whitehouse Station, NJ (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 362 days.

(21) Appl. No.: 14/872,468

(22) Filed: Oct. 1, 2015

(65) Prior Publication Data

US 2016/0115103 A1 Apr. 28, 2016

Related U.S. Application Data

(60) Provisional application No. 62/069,049, filed on Oct. 27, 2014.

(51) Int. Cl.
| | | |
|---|---|---|
| *C07C 2/86* | (2006.01) | |
| *C07C 5/27* | (2006.01) | |
| *C07C 51/265* | (2006.01) | |
| *C07C 7/163* | (2006.01) | |
| *C07C 7/12* | (2006.01) | |
| *C07C 45/00* | (2006.01) | |

(52) U.S. Cl.
CPC .............. *C07C 2/864* (2013.01); *C07C 2/865* (2013.01); *C07C 5/2702* (2013.01); *C07C 5/2732* (2013.01); *C07C 7/12* (2013.01); *C07C 7/163* (2013.01); *C07C 45/006* (2013.01); *C07C 51/265* (2013.01)

(58) Field of Classification Search
CPC ....... C07C 15/08; C07C 2/864; C07C 45/006; C07C 51/265; C07C 5/2702; C07C 5/2732; C07C 7/12; C07C 7/163; C07C 49/303; C07C 63/26; C07C 2/865
See application file for complete search history.

(56) References Cited

U.S. PATENT DOCUMENTS

| | | |
|---|---|---|
| 2,552,268 A | 5/1951 | Emerson et al. |
| 3,686,343 A | 8/1972 | Bearden, Jr. et al. |
| 3,702,886 A | 11/1972 | Argauer et al. |
| 3,709,979 A | 1/1973 | Chu |
| 3,832,449 A | 8/1974 | Rosinski et al. |
| 3,965,207 A | 6/1976 | Weinstein |
| 4,016,218 A | 4/1977 | Haag et al. |
| 4,016,245 A | 4/1977 | Plank et al. |
| 4,076,842 A | 2/1978 | Plank et al. |
| 4,255,606 A | 3/1981 | Tse |
| 4,300,014 A | 11/1981 | Yamasaki et al. |
| 4,356,338 A | 10/1982 | Young |
| 4,375,573 A | 3/1983 | Young |
| 4,377,718 A | 3/1983 | Sato et al. |
| 4,670,616 A | 6/1987 | De Simone et al. |
| 5,110,776 A | 5/1992 | Chitnis et al. |
| 5,231,064 A | 7/1993 | Absil et al. |
| 5,348,643 A | 9/1994 | Absil et al. |
| 7,453,018 B2 | 11/2008 | Dakka et al. |
| 8,252,967 B2 | 8/2012 | Hagemeister et al. |
| 8,502,008 B2 | 8/2013 | Kinn et al. |
| 8,507,744 B2 | 8/2013 | Hagemeister et al. |
| 8,529,757 B2 | 9/2013 | Go et al. |
| 8,541,639 B2 | 9/2013 | Ou et al. |
| 8,569,559 B2 | 10/2013 | Ou |
| 8,692,044 B2 | 4/2014 | Ou et al. |
| 8,697,929 B2 | 4/2014 | Ou et al. |
| 8,716,541 B2 | 5/2014 | Ou |
| 9,295,962 B2 * | 3/2016 | Zheng ..................... C07C 2/864 |
| 2011/0137099 A1 | 6/2011 | Ghosh et al. |
| 2012/0273392 A1 | 11/2012 | Serban et al. |
| 2012/0316375 A1 | 12/2012 | Zheng et al. |
| 2013/0324780 A1 | 12/2013 | Ou et al. |
| 2016/0115094 A1 | 4/2016 | Dakka et al. |

FOREIGN PATENT DOCUMENTS

| | | |
|---|---|---|
| JP | S58164527 | 9/1983 |
| WO | 00/40527 | 7/2000 |
| WO | 2012/074613 | 6/2012 |
| WO | 2012/134552 | 10/2012 |
| WO | 2013/180888 A | 12/2013 |

OTHER PUBLICATIONS

Wydra et al. Chemie Ingenieur Technik (74) 6 pages 800-804 (Year: 2002).*

Liu et al., "*Selective Phenol Hydrogenation to Cyclohexanone Over a Dual Supported Pd-Lewis Acid Catalyst*", Science, Nov. 27, 2009, vol. 326, pp. 1250-1252.

(Continued)

*Primary Examiner* — Sharon Pregler

(74) *Attorney, Agent, or Firm* — Kristian Sullivan; Priya G. Prasad

(57) ABSTRACT

A method for the purification of an aromatic hydrocarbon process stream having phenol therein is disclosed. Aspects of the method include contacting at least a portion of the aromatic hydrocarbon process stream with a hydrogenation catalyst under hydrogenation conditions to provide a hydrogenation effluent having a lower concentration of phenol than said aromatic hydrocarbon process stream.

23 Claims, 1 Drawing Sheet

(56) References Cited

OTHER PUBLICATIONS

Wang et al., "*Highly Selective Hydrogenation of Phenol and Derivatives over a Pd-Carbon Nitride Catalyst in Aqueous Media*", Journal of the American Chemical Society, 2011, vol. 133, pp. 2362-2365.
Group Notation Revised in Periodic Table, Chemical and Engineering New, 63(5), 1985, pp. 26-27.
Dimian et al., "Phenol Hydrogenation to Cyclohexanone", Chemical Process Design: Computer-Aided Case Studies, Wiley-VCH Verlag GmbH & Co. KGaA, Weinheim, 2008, pp. 129-172.
Kirk-Othmer, "Encyclopedia of Chemical Technology", 1979, Third Edition, vol. 7, pp. 410-416.
Dodgson et at, "A Low Cost Phenol to Cyclohexanone Process", Chemistry & Industry, 1989, pp. 830-833.
Non-Final Office Action for U.S. Appl. No. 14/872,388, dated Apr. 18, 2017, 26 pages.
Combined Search Report and Written Opinion for PCT/US2016/047027, dated Nov. 16, 2016, 14 pages.

\* cited by examiner

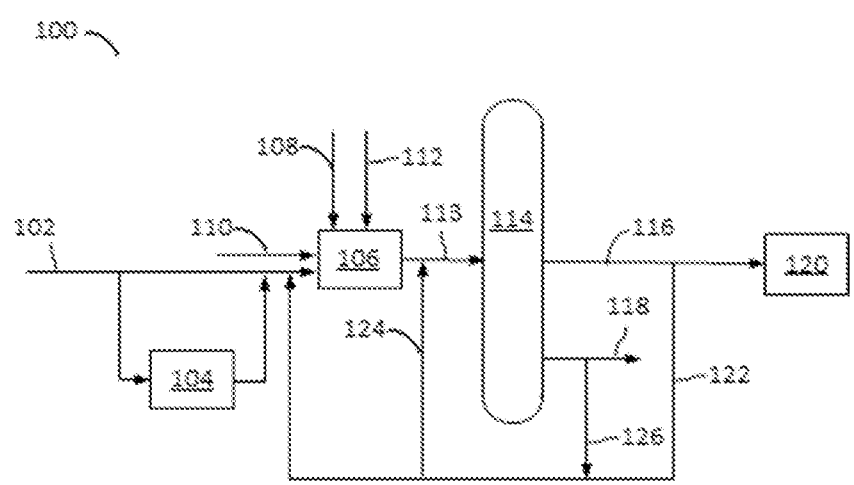

METHOD OF MAKING AROMATIC HYDROCARBONS

CROSS-REFERENCE OF RELATED APPLICATIONS

This application claims the benefit of Provisional Application No. 62/069,049, filed Oct. 27, 2014.

FIELD OF INVENTION

The invention is directed to purification of an aromatic hydrocarbon process stream including selective conversion of phenol from a stream comprising aromatic hydrocarbon mixtures.

BACKGROUND OF INVENTION

Of the aromatic $C_8$ isomers, including the three xylene isomers and ethylbenzene, paraxylene is of particularly high value since paraxylene is useful in the manufacture of terephthalic acid, used in synthetic fibers and resins. Refinery and chemical plant streams containing the aromatic $C_8$ isomers typically contain, at thermodynamic equilibrium, only is about 22-24 wt % paraxylene, based on the weight of the xylene isomers in the stream.

Separation of paraxylene from the other $C_8$ isomers requires superfractionation and/or multistage refrigeration steps and/or adsorptive separation, all of which are energy intensive.

One known method for producing paraxylene selectively involves the alkylation of toluene and/or benzene with methanol and/or dimethyl ether (DME) over a solid acid catalyst. Selectivities to paraxylene in excess of 90 wt % (based on total $C_8$ aromatic product) have been reported by reacting toluene with methanol in the presence of a catalyst comprising a porous crystalline material, preferably a medium-pore zeolite and particularly ZSM-5, having a Diffusion Parameter for 2,2 dimethylbutane of about 0.1-15 $sec^{-1}$ when measured at a temperature of 120° C. and a 2,2 dimethylbutane pressure of 60 torr (8 kPa).

It has been discovered that the production of paraxylene by toluene alkylation, however, can produce oxygenates, e.g., phenol, which act as free-radical reaction inhibitors in the subsequent oxidative conversion of paraxylene to terephthalic acid. Thus, the presence of such oxygenates in the paraxylene stream can substantially increase the reaction time of the paraxylene oxidation.

A method of deactivating such free-radical inhibitors in the paraxylene stream would be beneficial. A method wherein the free-radical inhibitors are converted to free-radical initiators to promote the subsequent oxidation reaction would also be beneficial.

SUMMARY OF INVENTION

It has been found that deleterious effects on downstream processes of the presence of oxygenate free-radical reaction inhibitors in the paraxylene stream may be reduced by converting the oxygenates to a ketone form, e.g., phenol to cyclohexanone. Surprisingly, the conversion may be performed in a single reactor with a combined alkylation and hydrogenation catalyst to provide both the aromatic alkylation and the selective oxygenate hydrogenation. While the alkylation and hydrogenation may be sequentially performed, a benefit of the present invention is that by careful selection and modification of the alkylation and hydrogenation catalysts, the hydrogenation of the oxygenate may be performed in the same reactor as the alkylation reaction without unacceptable loss in paraxylene production.

Thus in one aspect, the invention provides a method for the purification of an aromatic hydrocarbon process stream comprising paraxylene and phenol. At least a portion of the aromatic hydrocarbon process stream is contacted with a hydrogenation catalyst under hydrogenation conditions to provide a hydrogenation effluent having a lower concentration of is phenol than the aromatic hydrocarbon process stream.

In another aspect, the invention provides a method for producing paraxylene in which a feedstock comprising ≥5.0 wt % toluene and/or benzene, based on the weight of the feedstock, is contacted with a first mixture comprising ≥10.0 wt % of at least one oxygenate selected from methanol, dimethyl ether, and mixtures thereof, in an alkylation reactor in the presence of an alkylation catalyst to produce an aromatic hydrocarbon process stream comprising phenol and ≥25.0 wt % paraxylene. At least a portion of the aromatic hydrocarbon process stream is then contacted with a hydrogenation catalyst under hydrogenation conditions to provide a hydrogenation effluent having a lower concentration of phenol than the aromatic hydrocarbon process stream.

In yet another aspect, the invention provides a method for producing paraxylene in which a feedstock comprising ≥5.0 wt % toluene and/or benzene, based on the weight of the feedstock, is contacted with a first mixture comprising ≥10.0 wt % of at least one oxygenate selected from methanol, dimethyl ether, and mixtures thereof, in the presence of a combined alkylation and hydrogenation catalyst in a single reactor to produce an aromatic hydrocarbon process stream comprising ≥25.0 wt % paraxylene and phenol in a concentration of ≤1000.0 ppm.

BRIEF DESCRIPTION OF THE DRAWINGS

FIG. 1 schematically illustrates a combined alkylation/hydrogenation process according to an aspect of the invention.

DETAILED DESCRIPTION

According to aspects of the invention, there is provided a method for the purification of an aromatic hydrocarbon process stream comprising paraxylene and phenol. The method includes contacting an aromatic hydrocarbon process stream with a hydrogenation catalyst under hydrogenation conditions to provide a hydrogenation effluent having a lower concentration of phenol than the aromatic hydrocarbon process stream. The aromatic hydrocarbon process stream comprises an effluent stream of a toluene alkylation process, e.g., comprising C8 aromatics, particularly paraxylene, more particularly where the paraxylene is present in higher than equilibrium amounts. The toluene alkylation and phenol hydrogenation may be performed sequentially or contemporaneously. Thus, in particular aspects, process the toluene alkylation is performed in the presence of a hydrogenation catalyst that hydrogenates the phenol by-product formed during the alkylation.

For the purposes of this invention and the claims thereto, the new numbering scheme for the Periodic Table Groups is used as described in Chemical and Engineering News, 63(5), p. 27 (1985). Therefore, a "Group 4 metal" is an element from Group 4 of the Periodic Table, e.g., Hf, Ti, or Zr.

As used herein, references to a "reactor" shall be understood to include both distinct reactors as well as reaction zones within a single reactor apparatus. In other words and as is common, a single reactor may have multiple reaction zones. Where the description refers to a first and second reactor, the person of ordinary skill in the art will readily recognize such reference includes a single reactor having first and second reaction zones. Likewise, a first reactor effluent and a second reactor effluent will be recognized to include the effluent from the first reaction zone and the second reaction zone of a single reactor, respectively.

As used herein, the phrase "at least a portion of" means >0 to 100.0 wt % of the process stream or composition to which the phrase refers.

As used herein, the term "first mixture" means a hydrocarbon-containing composition including one or more oxygenates. Typically, the first mixture comprises ≥10.0 wt % of at least one oxygenate, based on the weight of the first mixture, preferably ≥about 50.0 wt %, more preferably ≥about 90.0 wt %, and most preferably ≥about 99.0 wt %. Ranges expressly disclosed include combinations of any of the above-enumerated values; e.g., ≥10.0 to about 100.0 wt %, about 12.5 to about 99.5 wt %, about 20.0 to about 90.0, about 50.0 to about 99.0 wt %, etc.

As used herein, the term "oxygenate," "oxygenate composition," and the like refer to oxygen-containing compounds having 1 to about 50 carbon atoms, preferably 1 to about 20 carbon atoms, more preferably 1 to about 10 carbon atoms, and most preferably 1 to about 4 carbon atoms. Exemplary oxygenates include alcohols, ethers, carbonyl compounds, e.g., aldehydes, ketones and carboxylic acids, and mixtures thereof. Particular oxygenates methanol, ethanol, dimethyl ether, diethyl ether, methylethyl ether, di-isopropyl ether, dimethyl carbonate, dimethyl ketone, formaldehyde, and acetic acid.

In any aspect, the oxygenate comprises one or more alcohols, preferably alcohols having 1 to about 20 carbon atoms, more preferably 1 to about 10 carbon atoms, or most preferably 1 to about 4 carbon atoms. The alcohols useful as first mixtures may be linear or branched, substituted or unsubstituted aliphatic alcohols and their unsaturated counterparts. Non-limiting examples of such alcohols include methanol, ethanol, propanols (e.g., n-propanol, isopropanol), butanols (e.g., n-butanol, sec-butanol, tert-butyl alcohol), pentanols, hexanols, etc., and mixtures thereof. In any aspect described herein, the first mixture may be one or more of methanol, and/or ethanol, particularly methanol. In any aspect, the first mixture may be methanol and dimethyl ether.

The oxygenate, particularly where the oxygenate comprises an alcohol (e.g., methanol), may optionally be subjected to dehydration, e.g., catalytic dehydration over e.g., γ-alumina Further optionally, at least a portion of any methanol and/or water remaining in the first mixture after catalytic dehydration may be separated from the first mixture. If desired, such catalytic dehydration may be used to reduce the water content of reactor effluent before it enters a subsequent reactor or reaction zone, e.g., second and/or third reactors as discussed below.

In any aspect, one or more other compounds may be present in first mixture. Typically, although not necessarily, such compounds include one or more heteroatoms other than oxygen. Some such compounds include amines, halides, mercaptans, sulfides, and the like. Particular such compounds include alkyl-mercaptans (e.g., methyl mercaptan and ethyl mercaptan), alkyl-sulfides (e.g., methyl sulfide), alkyl-amines (e.g., methyl amine), and alkyl-halides (e.g., methyl chloride and ethyl chloride). In any aspect, the first mixture includes one or more of ≥1.0 wt % acetylene, pyrolysis oil or aromatics, particularly $C_6$ and/or $C_7$ aromatics.

Alkylation Process

The alkylation process for forming the aromatic hydrocarbon stream can employ any aromatic feedstock comprising ≥5.0 wt % toluene and/or benzene, although in general it is preferred that the aromatic feed contains at least 90 wt %, especially at least 99 wt %, of benzene, toluene or a mixture thereof. An aromatic feed containing at least 99 wt % toluene is particularly desirable. Similarly, although the composition of the methanol-containing feed, i.e., first mixture, is not critical, it is generally desirable to employ feeds containing at least 90 wt %, especially at least 99 wt %, of methanol.

The catalyst employed in the alkylation process is generally a porous crystalline material and, in one preferred aspect, is a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient ($cm^2$/sec) and r is the crystal radius (cm). The diffusion parameter can be derived from sorption measurements provided the assumption is made that the plane sheet model describes the diffusion process. Thus for a given sorbate loading Q, the value $Q/Q_{eq}$, where $Q_{eq}$ is the equilibrium sorbate loading, is mathematically related to $(Dt/r^2)^{0.5}$ where t is the time (sec) required to reach the sorbate is loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one aspect, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described in U.S. Pat. No. 4,076,842. Zeolite ZSM-35 and the conventional preparation thereof are described in U.S. Pat. No. 4,016,245. ZSM-48 and the conventional preparation thereof are taught by U.S. Pat. No. 4,375,573. The entire disclosures of these U.S. patents are incorporated herein by reference.

In addition to the medium-pore size aluminosilicate zeolites, other medium pore acidic metallosilicates, such as silicoaluminophosphates (SAPOs), can be used in the present process. Non-limiting examples of zeolites useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56.

The medium pore zeolites described above are preferred for the present process since the size and shape of their pores favor the production of p-xylene over the other xylene isomers. However, conventional forms of these zeolites have Diffusion Parameter values in excess of the 0.1-15 sec$^{-1}$ range desired for the present process. Nevertheless, the required diffusivity can be achieved by severely steaming the zeolite so as to effect a controlled is reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired reduction in the micropore volume of the porous crystalline material can be effected by heating the material in the presence of steam at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups 2, 3, 4, 5, 13, 14, 15, and 16 of the Periodic Table. Conveniently, said at least one oxide modifier is selected from oxides of boron, magnesium, calcium, lanthanum and preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, such as between about 0.1 and about 10 wt %, based on the weight of the final catalyst.

Where the modifier includes phosphorus, incorporation of modifier in the alkylation catalyst is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Such phosphorous-stabilized catalyst compositions are well-known to provide hydrothermal stability. The phosphorous can be incorporated after formulation of the zeolite (such as by extrusion) to form self-bound catalyst particles. Optionally, a self-bound catalyst can be steamed after extrusion. Such compositions are particularly useful where the reactor is feed includes a significant amount of water, e.g., ≥5 wt % $H_2O$.

Representative phosphorus-containing compounds which may be used to incorporate a phosphorus oxide modifier into the catalyst of the invention include derivatives of groups represented by $PX_3$, $RPX_2$, $R_2PX$, $R_3P$, $X_3PO$, $(XO)_3PO$, $(XO)_3P$, $R_3P=O$, $R3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2PDX$, such as diethylphosphinous acid, primary, $(RO)P(OX)_2$, secondary, $(RO)_2PDX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphoro-chloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds which may be used to incorporate a boron oxide modifier into the catalyst of the invention include boric acid, trimethylborate, is boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of the invention may be combined with a variety of binder or matrix materials resistant to the temperatures and other conditions employed in the process. Such materials include active and inactive materials such as clays, silica and/or metal oxides such as alumina The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, is or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

The alkylation process can be conducted in any known reaction vessel but generally the methanol and aromatic feeds are contacted with the catalyst described above with the catalyst particles being disposed in one or more fluidized beds. Each of the methanol and aromatic feeds can be injected into the fluidized catalyst in a single stage. However, in one aspect, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

The conditions employed in the alkylation stage of the present process are not particularly constrained. Generally in the case of the methylation of toluene, the temperature is between about 500 and about 750° C., preferably between about 500 and about 700° C., and more preferably between about 500 and about 600° C. The alkylation may be conducted at any useful pressure. Typically the pressure is between about 1 atmosphere and about 1000 psig (between about 100 and about 7000 kPa), preferably between about 10 psig and about 200 psig (between about 170 and about 1480 kPa). The molar ratio of aromatic molecules (e.g., toluene) to moles of methanol (moles toluene/moles methanol) is typically at least about 0.2, preferably from about 0.2 to about 20. The weight hourly space velocity ("WHSV") for is total hydrocarbon feed to the reactor(s) in the alkylation process is typically about 0.2 to about 1000, preferably about 0.5 to about 500 for the aromatic reactant, and preferably about 0.01 to about 100 for the combined methanol reagent stage flows, based on total catalyst in the reactor(s).

The effluent from the alkylation process typically comprises a mixture of aromatic molecules, particularly $C_{8+}$ aromatics and phenol. Typically the alkylation effluent comprises ≥about 25.0 wt % of aromatics, based on the weight the alkylation effluent. In any aspect, the alkylation effluent may comprise ≥about 25.0 wt % paraxylene based on the weight of the aromatics. For example, the amount of paraxylene in the aromatics of the hydrocarbon component of the product stream may be about 25.0 to 100.0 wt %, preferably about 30.0 to 100.0 wt %, and more preferably about 40.0 to 100.0 wt %. Ranges expressly disclosed include combinations of any of the above-enumerated values.

The alkylation effluent also comprises a minor amount of phenol. While the amount of phenol is not particularly limited, the presence of phenol acts as a free radical inhibit in subsequent reaction. Thus, lower amounts of phenol are preferred. In particular aspects, the amount of phenol is ≤about 25.0 ppmw, preferably ≤about 10.0 ppmw, more preferably ≤about 5.0 ppmw, most preferably ≤about 1.0 ppmw, and ideally ≤about 0.5 ppmw. Ranges of the amount of phenol in the alkylation effluent expressly disclosed include ranges bound by the upper and lower values of phenol content enumerated above, e.g., about 0.5 to about 25 ppm, about 0.5 to about 10.0 ppm, about 1.0 to about 5.0 ppm, etc.

Hydrogenation Process

In an aspect of the invention, the alkylation effluent is hydrogenated to convert at least a portion of the phenol contained therein to cyclohexanone. The hydrogenation may be carried out by any suitable process. Cyclohexanone can be conventionally prepared from phenol by catalytic hydrogenation in a phenol hydrogenation reactor using any known hydrogenation catalyst. The reaction can be carried out in the liquid phase or the vapor phase as described in Kirk-Othmer Encyclopedia of Chemical Technology, e.g., $3^{rd}$ Edition, Vol. 7 (1979) pp. 410-416; I. Dodgson et al. "A low Cost Phenol to Cyclohexanone Process", Chemistry & Industry 18 Dec. 1989, pp. 830-833; A. C. Dimian and C. S. Bildea "Chemical Process Design, Computer-Aided Case Studies", Wiley-VCH Verlag GmbH&Co. KGaA, Weinheim, Germany, Chapter 5, pp. 129-172; or M. T. Musser "Cyclohexanol and Cyclohexanone", Ullmann's Encyclopedia of Industrial Chemistry (7th Edition, 2007), each of which is incorporated herein by reference. The use of a fixed-bed, moving-bed, or fluid bed reactor is envisioned.

The reaction method when carrying out the present invention may be any of a batch method, a semi-batch method or a continuous flow method. With the catalyst being in a solid state, the form of reaction may be any of liquid phase, vapor phase, liquid-vapor mixed phase, solid phase, or supercritical fluid phase, or any combination of these may be used. For example, with the catalyst being in a solid state, the reaction may be carried out in any form out of liquid-vapor mixed phase, solid-liquid-vapor mixed phase, liquid-supercritical fluid mixed phase or supercritical fluid phase. Furthermore, the reaction may be carried out under normal pressure or under a pressurized state. From the viewpoint of the reaction efficiency, using supercritical carbon dioxide is recommended, but the present invention is not limited thereto.

For example, in an aspect of the invention the effluent of the alkylation process may be contacted in the presence of a hydrogen source, e.g., $H_2$, with a hydrogenation catalyst comprising one or more catalytically active metals. A catalyst comprising at least one metallic element selected from the platinum group metals Pd, Os, Ir and Pt, or metallic elements such as Ni, Co, Fe, Zn, Cu, Mn, Pb, Cd, Cr, Ag, Au, Hg, Ga, In, Ge, Sn, Ti, Al and Si may be used. In particular aspects, the above-enumerated elements may be combined with a Group 2 elements Ca, Mg, Sr and Ba, and/or one or more alkali metals, e.g., Li, Na, K, Rb and Cs, particularly in combination with palladium, platinum, rhodium and/or ruthenium or alloying therewith can also be effectively used in the present invention. A catalyst comprising palladium is particularly useful in aspects of the invention.

In particular aspects, it may be desirable to reduce the activity of the catalyst to hydrogenate the paraxylene. Thus, additionally or alternatively, in any aspect the hydrogenation catalyst may include a paraxylene hydrogenation suppressing agent to suppress the hydrogenation of paraxylene. The suppressing agent is typically a metal different from the metal of the catalyst and may comprise one or more Group 8-Group 15 elements. Exemplary Group 8-Group 15 elements include Fe, Ru, Os, Co, Ru, Ir, Ni, Pd, Pt, Cu, Ag, Au, Zn, Cd, B, Al, Ga, In, C, Si, Ge, Sn, Pb, N, P, As, Sb, and Bi, particularly Fe, Sn, and/or Bi. Such catalysts are described in Int'l. App. No. WO 2012134552, incorporated herein by reference in its entirety.

In the present invention, for example, activated charcoal, alumina, magnesia, silica, silica alumina, zirconia, titania, zeolite, clay, kaolin, talc, bentonite, or a gel or sol thereof can be, but need not be, suitably used as a carrier in the supported rhodium and/or ruthenium catalyst. A mixture of suitable ones of these carriers may also be used in the catalyst. There are no particular limitations on the carrier, so long as the carrier does not is unacceptably hamper the reaction or the catalytic activity; even a carrier that exhibits some degree of catalytic activity toward the reaction can be used. Typically, the metal (other than metal associated with the support) is present in supported catalyst compositions at a concentration of 0.5-5 wt %, based on the total weight of the catalyst.

Typically, the hydrogenation catalyst is preferably activated before use by heat treatment in a stream of a gas such as hydrogen, nitrogen, argon, carbon dioxide, oxygen or air. The treatment temperature during the heating treatment is generally in a range of 50 to 700° C., preferably 80 to 600° C., more preferably 80 to 500° C., most preferably 100 to 500° C. A treatment temperature less than 50° C. is undesirable, since adsorbed matter will not be desorbed sufficiently. Moreover, a treatment temperature exceeding 700° C. is undesirable, since the structure of the carrier in the catalyst will become liable to break up, and hence the surface area will tend to drop, and moreover agglomeration of the metal particles will occur. The activation treatment time is influenced by the amount of matter adsorbed on the surface and the treatment temperature, and hence there are no particular limitations on this treatment time, although a treatment time of 0.1 to 100 hours is generally suitable.

In an aspect, the hydrogenation may be conducted as described by Liu et al., "Selective Phenol Hydrogenation to Cyclohexanone Over a Dual Supported Pd-Lewis Acid Catalyst, Science, Vol. 326, No. 5957, pp. 1250-1252 (November 2009). Alternatively, the effluent of the alkylation process may be passed over a hydrogenation catalyst as described by Wang et al., in "Highly Selective Hydrogenation of Phenol and Derivatives over a Pd-Carbon Nitride Catalyst in Aqueous Media,"*J. Am. Chem. Soc.,* 2011, Vol. 133, No. 88, pp. 2362-2365.

In another aspect, the hydrogenation may be carried out as described in U.S. Pat. No. 7,453,018, incorporated by reference herein in its entirety. In such a hydrogenation, the molecular sieve is modified by the addition of a hydrogenation component, wherein at least one of the following conditions is met: (a) the selectivated molecular sieve has an alpha value of less than 100 prior to the addition of the hydrogenation component, or (b) the selectivated and hydrogenated catalyst has an alpha value of less than 100.

The amount of the hydrogenation catalyst used is not critical. In the case of a batch reaction for example, the amount of the catalyst used relative to the phenol present in the effluent from the alkylation reaction may be in a range of 0.01 to 200 wt %, preferably 0.05 to 100 wt %, more preferably 0.05 to 50 wt %, yet more preferably 0.1 to 30 wt %, most preferably 0.1 to 10 wt %. The amount of the catalyst is set as appropriate in accordance with the reaction method, the reaction conditions, the types of the raw material and the catalyst, is and so on, but if the amount of the catalyst used is too low, then there will be a substantial drop in the progress of the reaction, and if the amount of the catalyst used is too high, then problems may arise such as the efficiency of contact and so on dropping, and the manufacturing cost increasing.

Additionally or alternatively, water may be fed into the reactor continuously or intermittently. The weight to weight ratio of water fed into the reactor to phenol fed into the reactor on average being 0.1 or less. Alumina support may be particularly suitable in aspects wherein water and the compound to be hydrogenated are fed into the reactor as a vapor. Activated carbon is in particular preferred where water and the compound to be hydrogenated are fed into the reactor as a liquid.

In any aspect, at least a portion of the effluent of the alkylation process may be provided to the reactor along with a co-feed. The co-feed is selected to increase selectivity of the catalyst toward phenol hydrogenation. Exemplary co-feeds include CO and $H_2S$.

The hydrogenation reaction is typically carried out at temperatures from about 25 to about 250° C. The temperature may be selected to balance the reaction rate, selectivity, and yield. The hydrogenation reaction is generally performed at a total pressure of about 0.1 to 150 MPa, preferably about 10 to about 150 MPa, and most preferably about 25 to 100 MPa. The reaction time is not particularly limited. Exemplary reaction times may be about 1 minute to 10 hours, preferably about 5 minutes to 5 hours, and more preferably about 5 minutes to about 2 hours. When carrying out the hydrogenation, there are no particular limitations on the composition charged in of the hydrogen and the phenol. High conversion ratios are generally improved by a relatively high molar ratio of hydrogen to phenol. Thus, in any aspect, the molar ratio of the hydrogen to the phenol is generally 1.0 to 1000.

The hydrogenation effluent typically comprises aromatics as described above. The phenol content of the hydrogenation effluent, however, is less than that of the alkylation effluent, based on the total weights of the alkylation and hydrogenation effluents. In any aspect, the hydrogenation effluent comprises ≤about 25.0 ppmw, preferably ≤about 10.0 ppmw, more preferably ≤about 5.0 ppmw, most preferably ≤about 1.0 ppmw, and ideally ≤about 0.5 ppmw. The hydrogenation effluent may also be characterized by the ratio of the amount of phenol therein to the amount of phenol in the alkylation effluent. In any aspect, the ratio of the wt % phenol in the hydrogenation effluent to the wt % of phenol in the alkylation effluent may be about 0.001 to about 0.95 wt %. Ranges of the ratio of the wt % phenol in the hydrogenation effluent to the wt % of phenol in the alkylation effluent expressly disclosed include ranges bound by the upper and lower values.

One skilled in the art will realize that because the phenol in the alkylation effluent is converted primarily to cyclohexanone, the hydrogenation effluent may comprise ≤about 25.0 ppmw cyclohexanone, preferably ≤about 10.0 ppmw, more preferably ≤about 5.0 ppmw, most preferably ≤about 1.0 ppmw, and ideally ≤about 0.5 ppmw.

Combined Alkylation/Hydrogenation

In another aspect of the invention, the aromatic feedstock is provided to a reaction vessel that includes, in addition to an alkylation catalyst above, a hydrogenation catalyst described above. In such aspects, generally, the reaction parameters, i.e., temperature, pressure, WHSV, etc., of the alkylation reaction are used. A hydrogen source is co-fed along with the oxygenate, i.e., methanol, and the aromatic feedstock, i.e., toluene, benzene or mixtures thereof.

The hydrogenation metal catalyst may be added to the alkylation catalyst to form a combined multifunctional catalyst that simultaneously hydrogenates phenol as the phenol is produced in the alkylation reaction. The combined alkylation/hydrogenation catalyst has the added benefit of improving the catalyst stability by hydrogenating reaction intermediates that are coke precursors. To prevent the hydrogenation of paraxylene, a paraxylene hydrogenation suppressing agent as described above may be included in the catalyst. Additionally, in any aspect of the combined alkylation/hydrogenation, a phenol hydrogenation selectivity co-feed, e.g. CO and $H_2S$, may be provided as described above. In the absence of providing a phenol hydrogenation selectivity co-feed, there may still be a phenol hydrogenation selectivity effect from CO formed from methanol decomposition in the reactor.

The effluent from the combined alkylation/hydrogenation process may comprise a mixture of aromatic molecules, particularly $C_{8+}$ aromatics and phenol. Typically the alkylation/hydrogenation effluent comprises ≥about 25.0 wt % of aromatics, based on the weight the alkylation/hydrogenation effluent. In any aspect, the alkylation/hydrogenation effluent may comprise ≥about 25.0 wt % paraxylene based on the weight of the aromatics. For example, the amount of paraxylene in the aromatics of the hydrocarbon component of the product stream may be about 25.0 to 100.0 wt %, preferably about 30.0 to 100.0 wt %, and more preferably about 40.0 to 100.0 wt %. Ranges expressly disclosed include combinations of any of the above-enumerated values.

The effluent from the combined alkylation/hydrogenation process may also have a phenol content of ≤about 25.0 ppmw, preferably ≤about 10.0 ppmw, more preferably ≤about 5.0 ppmw, most preferably ≤about 1.0 ppmw, and ideally ≤about 0.5 ppmw. Ranges is of the amount of phenol in the alkylation effluent expressly disclosed include ranges bound by the upper and lower values of phenol content enumerated above, e.g., about 0.5 to about 25 ppm, about 0.5 to about 10.0 ppm, about 1.0 to about 5.0 ppm, etc.

Likewise, the effluent from the combined alkylation/hydrogenation may have a cyclohexanone content of comprise ≤about 25.0 ppmw cyclohexanone, preferably ≤about 10.0 ppmw, more preferably ≤about 5.0 ppmw, most preferably ≤about 1.0 ppmw, and ideally ≤about 0.5 ppmw.

FIG. 1 schematically illustrates a process 100, an oxygenate-containing feed is provided via line 102 to optional dehydration unit 104 or to reactor 106. An aromatic feed is provided via line 108. Hydrogen may be supplied either to reactor 106 directly to the reactor via line 110 or it may be combined with one or more of lines 102, 108. Likewise the phenol hydrogenation selectivity co-feed may be provided to the reactor via line 112 or it may be combined with one or more of lines 102, 108, and 110.

Reactor 106 is operated under conditions suitable for alkylating the aromatics and hydrogenating the phenol byproduct as described above. Thus, reactor 106 has therein a catalyst composition suitable for alkylating the aromatics, i.e., toluene, in the aromatic feed with the oxygenate from line 102. Reactor 106 is typically a fluidized bed reactor.

Effluent from the combined alkylation/hydrogenation reactor 106 may be provided via line 113 to separation unit 114. Separation unit 114 may be any separation means or process suitable to separate paraxylene from the effluent. In one aspect, the separation unit 114 separates the effluent into an aromatics-enriched stream 116 and an aromatics-depleted stream 118, e.g., distillation tower, simulated moving-bed separation unit, high pressure separator, low pressure separator, flash drum, etc. The aromatics-enriched stream 116 comprises $C_{8+}$ aromatics, particularly paraxylene, metaxylene, orthoxylene, ethylbenzene. The aromatics-enriched stream 116 may be sent to recovery unit 120 to recover paraxylene the aromatics-enriched stream as is known in the art. Exemplary methods of purification may be described in one or more of U.S. Pat. Nos. 8,716,541; 8,697,929; 8,692,044; 8,569,559; 8,541,639; 8,529,757; 8,507,744; 8,502,008, each of which is incorporated herein by reference in its entirety.

In any aspect, at least a portion of the aromatics-enriched stream may be recycled directly or indirectly to reactor 106, e.g., via lines 122 and 102 as illustrated in the figure. Additionally or alternatively, at least a portion of the aromatics-enriched stream 116 may be recycled to separation unit 114, via line 124, or as may be otherwise convenient. Where the paraxylene in the aromatics-enriched stream is to be converted to terephthalic acid, the Is paraxylene recovered in recovery unit 120 preferably comprises at least a portion of the cyclohexanone of the effluent. The cyclohexanone acts as a free-radical promoter in the conversion of paraxylene to terephthalic acid. Thus, the combined alkylation/hydrogenation conveniently converts the problematic phenol into a beneficial additive.

Aromatics-depleted stream 118 may be treated in any convenient manner. In any aspect, aromatics-depleted stream 118 may be further separated in a second separation unit (not shown). Additionally or alternatively, at least a portion of the aromatics-depleted stream 118 may be recycled to the separation unit 114 via line 126, e.g., by combining with the portion of the aromatics-enriched portion in line 122. Additionally or alternatively, at least a portion of the aromatics-depleted portion may be returned, directly or indirectly to the process, directly or indirectly to reactor 106, e.g., via lines 122 and 102. Additionally or alternatively, at least a portion of the aromatics-depleted stream may be conducted away from the process 100 as is known in the art.

Particular Aspects

Aspect 1: A method for the purification of an aromatic hydrocarbon process stream comprising paraxylene and phenol, the method comprising contacting at least a portion of the aromatic hydrocarbon process stream with a hydrogenation catalyst under hydrogenation conditions to provide a hydrogenation effluent having a lower concentration of phenol than said aromatic hydrocarbon process stream.

Aspect 2: Aspect 1, wherein the hydrogenation effluent comprises ≥25.0 wt % paraxylene, e.g., 25.0 to 95.0 wt %, 20.0 to 80.0 wt %, 30.0 to 70.0 wt %, 40.0 to 60.0 wt %, 10.0 to 50.0 wt %, 20.0 to 60.0 wt %, 30.0 to 50.0 wt %.

Aspect 3: Any one of Aspects 1-2, wherein said aromatic hydrocarbon process stream comprises an alkylation process effluent comprising the products of a reaction of an oxygenate with benzene and/or toluene in the presence of an alkylation catalyst under alkylation conditions to provide said aromatic hydrocarbon process stream, wherein said oxygenate is selected from the group consisting of methanol, dimethyl ether, and mixtures thereof.

Aspect 4: Any one of aspects 1-3, wherein the aromatic hydrocarbon process stream is produced by the reaction of toluene and/or benzene with an oxygenate in the presence of an alkylation catalyst combined with the hydrogenation catalyst, said aromatic hydrocarbon process stream comprising ≥25.0 wt % paraxylene, e.g., 25.0 to 95.0 wt %, 20.0 to 80.0 wt %, 30.0 to 70.0 wt %, 40.0 to 60.0 wt %, 10.0 to 50.0 wt %, 20.0 to 60.0 wt %, 30.0 to 50.0 wt %, wherein said oxygenate is selected from the group consisting of methanol, dimethyl ether, and mixtures thereof.

Aspect 5: Any one of Aspects 1-4, further including providing a hydrogen source capable of hydrogenating the phenol in the presence of the hydrogenation catalyst.

Aspect 6: Any one of Aspects 1-5, wherein said hydrogenation effluent comprises <10.0 ppm of phenol, e.g., about 0.01 to about 10.0 ppmw, about 0.01 to about 9.0 ppmw, about 0.01 to about 8.0 ppmw, about 0.01 to about 7.0 ppmw, about 0.01 to about 6.0 ppmw, about 0.01 to about 5.0 ppmw, about 0.01 to about 4.0 ppmw, about 0.01 to about 3.0 ppmw, about 0.01 to about 2.0 ppmw, about 0.01 to about 1.0 ppmw, about 0.01 to about 0.5 ppmw, about 0.01 to about 0.05 ppmw.

Aspect 7: Any one of Aspects 1-6, wherein said contacting converts at least a portion of the phenol to cyclohexanone, optionally wherein said cyclohexanone is present in an amount ≤about 25.0 ppmw cyclohexanone, e.g., about 0.5 to about 25.0 ppmw, about 0.5 to about 10.0 ppmw, about 0.5 to about 7.5 ppmw, about 0.5 to about 5.0 ppmw, about 0.5 to about 2.5 ppmw, about 0.5 to about 1.0 ppmw, about 1.0 to about 25.0 ppmw, about 1.0 to about 10.0 ppmw, about 1.0 to about 7.5 ppmw, about 1.0 to about 5.0 ppmw, about 1.0 to about 2.5 ppmw, about 1.0 to about 2.5 ppmw, about 2.5 to about 25.0 ppmw, about 2.5 to about 10.0 ppmw, about 2.5 to about 7.5 ppmw, about 2.5 to about 5.0 ppmw.

Aspect 8: A method for producing paraxylene, the method comprising: (a) providing a feedstock comprising ≥5.0 wt % toluene and/or benzene, based on the weight of the feedstock; (b) contacting the feedstock in an alkylation reactor in the presence of an alkylation catalyst with a first mixture comprising ≥10.0 wt % of at least one oxygenate selected from the group consisting of methanol, dimethyl ether, and mixtures thereof, to produce an aromatic hydrocarbon process stream comprising phenol and ≥25.0 wt % paraxylene; and (c) contacting at least a portion of the aromatic hydrocarbon process stream with a hydrogenation catalyst under hydrogenation conditions to provide a hydrogenation effluent having a lower concentration of phenol than said aromatic hydrocarbon process stream.

Aspect 9: Aspect 8, wherein the hydrogenation effluent comprises ≥25.0 wt % paraxylene, e.g., 25.0 to 95.0 wt %, 20.0 to 80.0 wt %, 30.0 to 70.0 wt %, 40.0 to 60.0 wt %, 10.0 to 50.0 wt %, 20.0 to 60.0 wt %, 30.0 to 50.0 wt %.

Aspect 10: Any one of Aspects 8-9, wherein said contacting under hydrogenation conditions includes providing a hydrogen source capable of hydrogenating the phenol in the presence of the hydrogenation catalyst.

Aspect 11: Any one of Aspects 8-10, wherein said hydrogenation effluent is comprises ≤10 ppm of phenol, e.g., about 0.01 to about 10.0 ppmw, about 0.01 to about 9.0 ppmw, about 0.01 to about 8.0 ppmw, about 0.01 to about 7.0 ppmw, about 0.01 to about 6.0 ppmw, about 0.01 to about 5.0 ppmw, about 0.01 to about 4.0 ppmw, about 0.01 to about 3.0 ppmw, about 0.01 to about 2.0 ppmw, about 0.01 to about 1.0 ppmw, about 0.01 to about 0.5 ppmw, about 0.01 to about 0.05 ppmw.

Aspect 12: Any one of Aspects 8-11, wherein said contacting under hydrogenation conditions converts at least a portion of the phenol to cyclohexanone; optionally wherein said cyclohexanone is present in an amount ≤about 25.0 ppmw cyclohexanone, e.g., about 0.5 to about 25.0 ppmw, about 0.5 to about 10.0 ppmw, about 0.5 to about 7.5 ppmw, about 0.5 to about 5.0 ppmw, about 0.5 to about 2.5 ppmw, about 0.5 to about 1.0 ppmw, about 1.0 to about 25.0 ppmw, about 1.0 to about 10.0 ppmw, about 1.0 to about 7.5 ppmw, about 1.0 to about 5.0 ppmw, about 1.0 to about 2.5 ppmw, about 2.5 to about 25.0 ppmw, about 2.5 to about 10.0 ppmw, about 2.5 to about 7.5 ppmw, about 2.5 to about 5.0 ppmw.

Aspect 13: Any one of Aspects 8-12, further comprising separating from the hydrogenation effluent an aromatics-enriched stream and an aromatics-depleted stream, wherein the aromatics-enriched stream comprises $C_{8+}$ aromatics.

Aspect 14: Aspect 13, wherein the aromatics-enriched stream comprises one or more $C_{8+}$ aromatics selected from the group consisting of paraxylene, metaxylene, orthoxylene, ethylbenzene, particularly wherein paraxylene is present in an amount ≥25.0 wt % paraxylene, e.g., 25.0 to 95.0 wt %, 20.0 to 80.0 wt %, 30.0 to 70.0 wt %, 40.0 to 60.0 wt %, 10.0 to 50.0 wt %, 20.0 to 60.0 wt %, 30.0 to 50.0 wt %.

Aspect 15: Any one of Aspects 13-14, further comprising recovering at least a portion of the paraxylene from the aromatics-enriched stream.

Aspect 16: Any one of Aspects 13-15, further comprising separating an ethylbenzene-enriched stream the aromatics-enriched stream.

Aspect 17: Any one of Aspects 8-16, wherein said alkylation catalyst and said hydrogenation catalyst are combined into a multifunctional catalyst contained in a single reactor such that phenol produced during the alkylation reaction is simultaneously hydrogenated.

Aspect 18: A method for producing paraxylene, the method comprising: (a) providing a feedstock comprising ≥5.0 wt % toluene and/or benzene, based on the weight of the feedstock; and (b) contacting the feedstock in the presence of a combined alkylation and hydrogenation catalyst in a single reactor with a first mixture comprising ≥10.0 wt % of at is least one oxygenate selected from the group consisting of methanol, dimethyl ether, and mixtures thereof, to produce an aromatic hydrocarbon process stream comprising ≥25.0 wt % paraxylene, e.g., 25.0 to 95.0 wt %, 20.0 to 80.0 wt %, 30.0 to 70.0 wt %, 40.0 to 60.0 wt %, 10.0 to 50.0 wt %, 20.0 to 60.0 wt %, 30.0 to 50.0 wt %, and phenol in a concentration of ≤about 1000.0 ppmw, e.g., ≤about 500.0 ppmw, ≤about 250.0 ppmw, ≤about 100.0 ppmw, ≤about 50.0 ppmw, ≤about 25.0 ppmw, ≤about 10.0 ppmw, about 0.01 to about 10.0 ppmw, about 0.01 to about 9.0 ppmw, about 0.01 to about 8.0 ppmw, about 0.01 to about 7.0 ppmw, about 0.01 to about 6.0 ppmw, about 0.01 to about 5.0 ppmw, about 0.01 to about 4.0 ppmw, about 0.01 to about 3.0 ppmw, about 0.01 to about 2.0 ppmw, about 0.01 to about 1.0 ppmw, about 0.01 to about 0.5 ppmw, about 0.01 to about 0.05 ppmw.

Aspect 19: Aspect 18, wherein said contacting includes providing a hydrogen source capable of hydrogenating the phenol in the presence of the hydrogenation catalyst.

Aspect 20: Any one of Aspects 18-19, wherein said contacting converts at least a portion of the phenol to cyclohexanone; optionally wherein said cyclohexanone is present in an amount ≤about 25.0 ppmw cyclohexanone, e.g., about 0.5 to about 25.0 ppmw, about 0.5 to about 10.0 ppmw, about 0.5 to about 7.5 ppmw, about 0.5 to about 5.0 ppmw, about 0.5 to about 2.5 ppmw, about 0.5 to about 1.0 ppmw, about 1.0 to about 25.0 ppmw, about 1.0 to about 10.0 ppmw, about 1.0 to about 7.5 ppmw, about 1.0 to about 5.0 ppmw, about 1.0 to about 2.5 ppmw, about 2.5 to about 25.0 ppmw, about 2.5 to about 10.0 ppmw, about 2.5 to about 7.5 ppmw, about 2.5 to about 5.0 ppmw.

Aspect 21: Any one of Aspects 18-20, further comprising separating an aromatics-enriched stream and an aromatics-depleted stream from the effluent.

Aspect 22: Aspect 21, wherein the aromatics-enriched stream comprises $C_{8+}$ aromatics.

Aspect 23: Any one of Aspects 21-22, wherein the aromatics-enriched stream comprises one or more $C_{8+}$ aromatics selected from the group consisting of paraxylene, metaxylene, orthoxylene, ethylbenzene, particularly wherein paraxylene is present in an amount ≥25.0 wt % paraxylene, e.g., 25.0 to 95.0 wt %, 20.0 to 80.0 wt %, 30.0 to 70.0 wt %, 40.0 to 60.0 wt %, 10.0 to 50.0 wt %, 20.0 to 60.0 wt %, 30.0 to 50.0 wt %.

Aspect 24: Any one of Aspects 21-23, further comprising recovering paraxylene from the aromatics-enriched stream and/or providing the paraxylene to a process for converting paraxylene to terephthalic acid.

Aspect 25: Any one of Aspects 1-24, wherein the alkylation catalyst comprises a zeolite, particularly a ZSM-type catalyst, e.g., ZSM-5, ZSM-11, ZSM-12, ZSM-22, ZSM-23, is ZSM-35, and ZSM-48, with ZSM-5 and ZSM-11; and/or an silicoaluminophosphate (SAPO), e.g., SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56.

Aspect 26: Any one of Aspects 1-25, wherein the hydrogenation catalyst comprises Pd, Os, Ir and Pt, Ni, Co, Fe, Zn, Cu, Mn, Pb, Cd, Cr, Ag, Au, Hg, Ga, In, Ge, Sn, Ti, Al and Si; optionally further including Ca, Mg, Sr and Ba, and/or an alkali metals Li, Na, K, Rb and Cs, particularly in combination with palladium, platinum, rhodium and/or ruthenium.

Aspect 27: Any one of Aspects 1-26, wherein said hydrogenation catalyst further comprises a paraxylene hydrogenation suppressing agent.

Aspect 28: Any one of Aspects 1-27, wherein said contacting under hydrogenation conditions includes providing a co-feed to increase the selectivity of said hydrogenation catalyst to phenol hydrogenation.

Aspect 29: Aspect 27, wherein said paraxylene hydrogenation suppressing agent comprises a metal, different from the metal of the hydrogenation catalyst, selected from the group consisting of Pd, Os, Ir and Pt, Ni, Co, Fe, Zn, Cu, Mn, Pb, Cd, Cr, Ag, Au, Hg, Ga, In, Ge, Sn, Ti, Al and Si; optionally further including Ca, Mg, Sr and Ba, and/or an alkali metals Li, Na, K, Rb and Cs, particularly in combination with palladium, platinum, rhodium and/or ruthenium.

Aspect 30: Aspect 28, wherein the co-feed comprises CO or $H_2S$.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is not incorporated by reference herein. As is apparent from the foregoing general description and the specific aspects, while forms of the invention have been illustrated and described, various modifications can be made without departing from the spirit and scope of the invention. Accordingly, it is not intended that the invention be limited thereby. Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. Aspects of the invention include those that are substantially free of or essentially free of any element, step, composition, ingredient or other claim element not expressly recited or described.

What is claimed is:

1. A method for the purification of an aromatic hydrocarbon process stream comprising paraxylene and phenol, the method comprising contacting at least a portion of the aromatic hydrocarbon process stream with a hydrogenation catalyst under a set of conditions to provide a hydrogenation effluent having a lower concentration of phenol than said aromatic hydrocarbon process stream, wherein the set of conditions comprises a temperature between 500 and 750° C., a pressure between about 100 and 7000 kPa, and a weight hourly space velocity (WHSV) of about 0.2 to about 1000 $hr^{-1}$.

2. The method according to claim 1, wherein the hydrogenation effluent comprises ≥25.0 wt % paraxylene.

3. The method according to claim 1, wherein said aromatic hydrocarbon process stream comprises an alkylation process effluent comprising the products of a reaction of an oxygenate with toluene and/or benzene in the presence of an alkylation catalyst under the set of conditions to provide said aromatic hydrocarbon process stream, wherein said oxygenate is selected from the group consisting of methanol, dimethyl ether, and mixtures thereof.

4. The method according to claim 1, wherein said aromatic hydrocarbon process stream is produced by the reaction of toluene and/or benzene with an oxygenate in the presence of an alkylation catalyst combined with the hydrogenation catalyst under the set of conditions, wherein said aromatic hydrocarbon process stream comprises ≥25.0 wt % paraxylene, and wherein said oxygenate is selected from the group consisting of methanol, dimethyl ether, and mixtures thereof.

5. The method of claim 1, further including providing a hydrogen source capable of hydrogenating the phenol in the presence of the hydrogenation catalyst.

6. The method according to claim 1, wherein said effluent comprises ≤10 ppm of phenol.

7. The method of claim 1, wherein said contacting converts at least a portion of the phenol to cyclohexanone.

8. A method for producing paraxylene, the method comprising:
 (a) providing a feedstock comprising ≥5.0 wt % toluene and/or benzene, based on the weight of the feedstock;
 (b) contacting the feedstock in an alkylation reactor in the presence of an alkylation catalyst with a first mixture comprising ≥10.0 wt % of at least one oxygenate selected from the group consisting of methanol, dimethyl ether, and mixtures thereof under a set of conditions, to produce an aromatic hydrocarbon process stream comprising phenol and ≥25.0 wt % paraxylene; and
 (c) contacting at least a portion of the aromatic hydrocarbon process stream with a hydrogenation catalyst under the set of conditions to provide a hydrogenation effluent having a lower concentration of phenol than said aromatic hydrocarbon process stream,
 wherein the set of conditions comprises a temperature between 500 and 750° C., a pressure between about 100 and 7000 kPa, and a weight hourly space velocity (WHSV) of about 0.2 to about 1000 $hr^{-1}$.

9. The method of claim 8, wherein the hydrogenation effluent comprises ≥25.0 wt % paraxylene.

10. The method of claim 8, wherein said contacting under the set of conditions includes providing a hydrogen source capable of hydrogenating the phenol in the presence of the hydrogenation catalyst.

11. The method of claim 8, wherein said effluent comprises ≤1000 ppm of phenol.

12. The method of claim 8, wherein said contacting under the set of conditions converts at least a portion of the phenol to cyclohexanone.

13. The method of claim 8, further comprising (d) separating an aromatics-enriched stream and an aromatics-depleted stream from the hydrogenation effluent, wherein the aromatics-enriched stream comprises one or more $C_{8+}$ aromatics selected from the group consisting of paraxylene, metaxylene, orthoxylene, ethylbenzene; and (e) recovering paraxylene from the aromatics-enriched stream.

14. The method of claim 13, further comprising separating an ethylbenzene-enriched stream from the aromatics-enriched stream.

15. The method of claim 8, wherein said alkylation catalyst and said hydrogenation catalyst are combined into a multifunctional catalyst contained in a single reactor such that phenol produced during the alkylation reaction is simultaneously hydrogenated.

16. The method of claim 8, wherein said hydrogenation catalyst further comprises a paraxylene hydrogenation suppressing agent.

17. The method of claim 8, wherein said contacting under hydrogenation conditions includes providing a co-feed to increase the selectivity of said hydrogenation catalyst to phenol hydrogenation.

18. A method for producing paraxylene, the method comprising:
 (a) providing a feedstock comprising ≥5.0 wt % toluene and/or benzene, based on the weight of the feedstock; and
 (b) contacting the feedstock in the presence of a combined alkylation and hydrogenation catalyst in a single reactor with a first mixture comprising ≥10.0 wt% of at least one oxygenate selected from the group consisting of methanol, dimethyl ether, and mixtures thereof under a set of conditions, to produce an aromatic hydrocarbon process stream comprising ≥25.0 wt % paraxylene and phenol in a concentration of ≤1000.0 ppm, wherein the set of conditions comprises a temperature between 500 and 750° C., a pressure between about 100 and 7000 kPa, and a weight hourly space velocity (WHSV) of about 0.2 to about 1000 $hr^{-1}$.

19. The method of claim 18, wherein said contacting includes providing a hydrogen source capable of hydrogenating the phenol in the presence of the hydrogenation catalyst.

20. The method of claim 18, wherein said contacting converts at least a portion of phenol produced in the alkylation reaction to cyclohexanone.

21. The method of claim 18, further comprising (c) separating an aromatics-enriched stream and an aromatics-depleted stream from the aromatic hydrocarbon process stream, wherein the aromatics-enriched stream comprises one or more $C_{8+}$ aromatics selected from the group consisting of paraxylene, metaxylene, orthoxylene, ethylbenzene; and (d) recovering paraxylene from the aromatics-enriched stream.

22. The method of claim 18, wherein said hydrogenation catalyst further comprises a paraxylene hydrogenation suppressing agent.

23. The method of claim 18, wherein said contacting includes providing a co-feed to increase the selectivity of said hydrogenation catalyst to phenol hydrogenation.

\* \* \* \* \*